(12) United States Patent
Nichols et al.

(10) Patent No.: US 7,458,373 B2
(45) Date of Patent: *Dec. 2, 2008

(54) AEROSOL GENERATOR FOR DRUG FORMULATION

(75) Inventors: Walter A. Nichols, Chesterfield, VA (US); Donald L. Brookman, Richmond, VA (US); Gary E. Grollimund, Chesterfield, VA (US); Ulysses Smith, Midlothian, VA (US)

(73) Assignee: Philip Morris USA Inc., Richmond, VA (US)

( * ) Notice: Subject to any disclaimer, the term of this patent is extended or adjusted under 35 U.S.C. 154(b) by 1051 days.

This patent is subject to a terminal disclaimer.

(21) Appl. No.: 10/341,521

(22) Filed: Jan. 14, 2003

(65) Prior Publication Data
US 2003/0230303 A1 Dec. 18, 2003

Related U.S. Application Data

(60) Provisional application No. 60/347,872, filed on Jan. 15, 2002.

(51) Int. Cl.
*A61M 15/00* (2006.01)
(52) U.S. Cl. .............................. 128/203.15; 128/203.17
(58) Field of Classification Search ............ 128/200.23, 128/200.14, 203.15, 203.23, 203.17
See application file for complete search history.

(56) References Cited

U.S. PATENT DOCUMENTS

| | | | |
|---|---|---|---|
| 3,716,416 A | 2/1973 | Adlhart et al. | |
| 4,114,615 A * | 9/1978 | Wetterlin | 128/200.21 |
| 4,627,432 A | 12/1986 | Newell et al. | |
| 4,811,731 A | 3/1989 | Newell et al. | |
| 5,363,842 A | 11/1994 | Mishelevich et al. | |
| 5,487,378 A | 1/1996 | Robertson et al. | |
| 5,522,378 A | 6/1996 | Ritson et al. | |
| 5,622,162 A | 4/1997 | Johansson et al. | |
| 5,743,251 A | 4/1998 | Howell et al. | |
| 5,794,612 A | 8/1998 | Wachter et al. | |
| 5,839,430 A | 11/1998 | Cama | |

(Continued)

OTHER PUBLICATIONS

Notification of Transmittal of the International Search Report or the Declaration for PCT/US03/01048 dated Jul. 17, 2003.

(Continued)

*Primary Examiner*—Darwin P Erezo
(74) *Attorney, Agent, or Firm*—Buchanan Ingersoll & Rooney PC

(57) ABSTRACT

An aerosol generator such as a hand-held inhaler and method of delivering aerosol to a user inhaling on an outlet of a mouthpiece when a pressure drop is detected within the mouthpiece. A medicated fluid passing through a capillary passage is heated sufficiently to vaporize the fluid and form the aerosol by condensation of the vaporized fluid as it admixes with air. Air is supplied to the mouthpiece through an air passage which is initially closed during detection of the pressure drop. A metering chamber allows consistent delivery of precise doses of fluid to the capillary passage. The pressure drop is detected before air is supplied to the mouthpiece with the result that the aerosol can be quickly delivered to the user as the user begins to inhale on the mouthpiece. The quick delivery of aerosol provides more efficient use of the user's lung capacity.

32 Claims, 9 Drawing Sheets

U.S. PATENT DOCUMENTS

| | | | |
|---|---|---|---|
| 5,855,564 A * | 1/1999 | Ruskewicz | 604/62 |
| 5,881,715 A | 3/1999 | Shibasaki | |
| 5,894,841 A | 4/1999 | Voges | |
| 6,152,130 A | 11/2000 | Abrams et al. | |
| 6,155,268 A | 12/2000 | Takeuchi | |
| 6,230,706 B1 * | 5/2001 | Gonda et al. | 128/203.12 |
| 6,234,167 B1 | 5/2001 | Cox et al. | |
| 6,318,361 B1 | 11/2001 | Sosiak | |
| 6,516,796 B1 | 2/2003 | Cox et al. | |
| 6,528,018 B1 | 3/2003 | Berndt | |
| 6,557,552 B1 | 5/2003 | Cox et al. | |
| 6,854,461 B2 * | 2/2005 | Nichols et al. | 128/203.16 |

OTHER PUBLICATIONS

Written Opinion dated Jan. 17, 2006 for PCT/US03/01048.

* cited by examiner

US 7,458,373 B2

AEROSOL GENERATOR FOR DRUG FORMULATION

This application claims priority under 35 U.S.C. 119 to U.S. Provisional Application No. 60/347,872 entitled AEROSOL GENERATOR FOR DRUG FORMULATION and filed on Jan. 15, 2002, the entire content of which is hereby incorporated by reference.

BACKGROUND OF THE INVENTION

1. Field of the Invention

The present invention relates generally to aerosol generation. More specifically, the present invention relates to an aerosol generator which provides controlled doses of medicament to a patient during use.

2. Description of Related Art

Metered dose inhalers for delivering aerosol medication for inhalation by a patient are disclosed in U.S. Pat. Nos. 5,487,378; 5,522,378; 5,622,162; 5,794,612; 5,839,430; 5,894,841; and 6,152,130. Some inhalers use the propulsive force of a propellant system such as a mixture of liquified chlorofluorocarbons. Other inhalers use an ultrasonic nebulizer system to atomize a liquid in a carrier gas stream or a burst of inspired air to fluidize and draw a dose of powder into the bronchial tract. Commonly owned U.S. Pat. Nos. 5,743,251 and 6,234,167 disclose aerosol generators wherein a liquid formulation is vaporized to form an inhalation aerosol.

In order to trigger delivery of aerosol from an inhaler, various types of breath actuation systems have been proposed. According to U.S. Pat. No. 5,622,162, some breath actuation systems require a patient's inspiratory effort to move a mechanical lever or the detected flow to rise above a preset threshold. A problem with such systems is that inspiration varies from person to person and some patients are unable to generate sufficient flow to activate the unit. Although attempts have been made to improve breath actuation systems, detection is still based on air flow generated by the patient with the result that the patient inhales a volume of air before delivery of the aerosol occurs. As a result, the patient may not inhale a full dose of medication.

Other techniques are known for generating aerosols. For example, U.S. Pat. Nos. 4,811,731 and 4,627,432 disclose devices for administering medicaments to patients in which a capsule is pierced by a pin to release a medicament in powder form. A user then inhales the released medicament through an opening in the device.

SUMMARY OF THE INVENTION

According to a first embodiment, the invention provides an aerosol generator comprising a mouthpiece having an outlet through which aerosol is supplied to a user of the aerosol generator, an air passage through which air is supplied to an interior of the mouthpiece and a sensor detecting a pressure drop in the interior of the mouthpiece.

The aerosol generator can include a housing, a capillary passage disposed within the housing, a heater disposed within the housing, a reservoir disposed within the housing, a metering chamber disposed within the housing, the metering chamber being supplied fluid from the reservoir by a first flow passage and the capillary passage being supplied fluid from the metering chamber by a second flow passage, a power source adapted to supply electrical power to the heater, a first valve adapted to open and close the first flow passage, a second valve adapted to open and close the second flow passage and a third valve adapted to open and close the air passage. The valves can be opened and closed by a motor and a camshaft, the camshaft including a plurality of camshaft lobes operatively associated with the first, second and third valves, the camshaft lobes being operable to close the first valve and open the second and third valves during an aerosol delivery cycle in which fluid is supplied to the capillary passage. The camshaft lobes open the first valve and close the second and third valves during a fill cycle in which fluid is supplied to the metering chamber. A stepper motor can be operatively coupled with the camshaft wherein the stepper motor rotates the camshaft to open and close the first, second and third valves. The reservoir can be removably attached to the housing and/or the reservoir can include a piston operable to pressurize fluid in the reservoir.

According to a preferred embodiment, the housing can include a cap slidably attached to the housing, the cap including the mouthpiece at one end thereof. Further, a liquid crystal display can be located on a portion of the housing which is exposed when the cap is moved to an aerosol delivery position. The sensor is preferably operable to send a controller a signal when the user inhales on the outlet of the mouthpiece. The sensor can comprise a transducer which detects a pressure drop in the interior of the mouthpiece when the user inhales on the outlet of the mouthpiece. The controller can be used to monitor a parameter of the heater and deliver power from the power supply to the heater such that the heater is maintained at a desirable temperature range during the aerosol delivery cycle.

In another preferred embodiment, the aerosol generator is a hand-held inhaler, the interior of the mouthpiece is supplied air only through the air passage, and the aerosol generator includes a valve which opens the air passage within a predetermined time period after the user inhales on the outlet.

According to a second embodiment, an aerosol generator comprises a mouthpiece having an outlet through which aerosol is supplied to a user of the aerosol generator, an aerosol generator system operable to supply aerosol to an interior of the mouthpiece, an air passage through which air is supplied to the interior of the mouthpiece, a pressure sensor operable to output a signal upon detection of a drop in pressure in the interior of the mouthpiece, a controller operable to activate the aerosol generator system to deliver aerosol to the interior of the mouthpiece in response to output of the signal by the pressure sensor, and a valve operable to open and close the air passage, the controller being operable to open the valve in response to output of the signal by the pressure sensor. The aerosol generator system can comprise a propellant-based aerosol generator, a nebulizer-based aerosol generator or a vaporized-based aerosol generator.

According to the second embodiment, the aerosol generator can include a housing and a cap slidably attached to the housing, the cap including the mouthpiece at one end thereof, the cap being slidable from an off position at which aerosol is prevented from being delivered to the interior of the mouthpiece to an aerosol delivery position at which the aerosol generating system is in a breath actuation mode wherein the user can obtain a dose of aerosol by inhaling on the outlet. Preferably, the aerosol generator comprises a hand-held inhaler and the aerosol generating system comprises a capillary sized flow passage and a heater arranged to volatilize liquid in the flow passage so as to produce the aerosol in the interior of the mouthpiece. The aerosol generator can further comprise a dispensing member and a metering chamber, the metering chamber comprising a recess and an elastomeric wall covering the recess, the dispensing member being movable from a first position relative to the elastomeric wall to a second position at which the elastomeric wall is deformed into the recess, the metering chamber providing fluid communication between a source of fluid and the flow passage, and the dispensing member being movable in a manner which provides a substantially constant flow rate of the fluid in the flow passage.

In a third embodiment, the aerosol generator includes a metering chamber comprising a recess in a first layer of material and an elastomeric layer overlying the recess, a dispensing member movable from a first position relative to the elastomeric layer to a second position at which the elastomeric layer is deformed into the recess, a flow passage in fluid communication with the metering chamber, a mouthpiece having an interior thereof in fluid communication with an outlet of the flow passage, and a heater in heat transfer communication with at least a portion of the flow passage, the heater being operable to volatilize fluid in the flow passage such that volatilized fluid forms an aerosol in the interior of the mouthpiece.

According to the third embodiment, a controller can be used to electrically operate an actuating mechanism which moves the dispensing member from the first position to the second position so as to provide a substantially constant flow rate of a predetermined volume of fluid through the flow passage. The flow passage is preferably a capillary sized flow passage and the first layer of material can include an outlet, a first channel extending between the inlet and the metering chamber, an outlet and a second channel extending between the metering chamber and the outlet, the elastomeric layer covering the inlet, the first channel, the second channel and the outlet. First and second plungers can be used to open and close the inlet and outlet, the first plunger being movable from a first position at which the inlet is open to a second position at which the elastomeric layer is pressed against a first valve seat so as to close the inlet, and the second plunger being movable from a first position at which the outlet is open to a second position at which the elastomeric layer is pressed against a second valve seat so as to close the outlet. An actuating mechanism can be used to move the first plunger to the second position while maintaining the second plunger in the first position.

In a fourth embodiment, the invention provides a method for generating an aerosol with an aerosol generator having a mouthpiece through which aerosol is delivered to a user, the method comprising sensing a pressure drop in an interior of the mouthpiece when the user inhales on an outlet of the mouthpiece, supplying aerosol to the interior of the mouthpiece when the pressure drop is detected and supplying air to the interior of the mouthpiece by opening an air passage when the pressure drop is detected.

In a preferred embodiment, the aerosol generator comprises a hand-held inhaler having a slidable cap, the method further comprising sliding the cap from a closed position to an open position, the open position activating components of the aerosol generator to deliver aerosol to the user when the pressure drop is detected. The aerosol generator preferably includes a heater and a capillary passage, the heater heating the capillary passage sufficiently to volatilize fluid therein, the volatilized fluid admixing with air and forming the aerosol. The aerosol generator can include a controller which monitors a parameter of the heater and controls supply of power to the heater to maintain the heater at a desired temperature range while fluid passes through the capillary passage, the fluid being volatilized so as to form the aerosol.

In a preferred method, the aerosol generator includes a housing, a capillary passage disposed within the housing, the capillary passage having an outlet in fluid communication with the interior of the mouthpiece, a heater disposed within the housing, a reservoir disposed within the housing, a metering chamber disposed within the housing, the metering chamber being supplied fluid from the reservoir by a first flow passage and the capillary passage being supplied fluid from the metering chamber by a second flow passage, a power source adapted to supply electrical power to the heater, a first valve adapted to open and close the first flow passage, a second valve adapted to open and close the second flow passage, a third valve adapted to open and close the air passage, the aerosol being supplied to the interior of the mouthpiece by supplying power to the heater, closing the first valve, opening the second and third valves, removing fluid from the metering chamber, supplying a predetermined volume of fluid to the capillary passage and volatilizing the fluid in the capillary passage. A motor driven camshaft can be used to open and close the first, second and third valves by rotating the camshaft to a first position at which the first valve is closed and the second and third valves are open to effect delivery of a predetermined volume of fluid to the capillary passage during an aerosol delivery cycle, and further rotating the camshaft to a second position at which the second and third valves are closed and the first valve opens to effect delivery of fluid from the reservoir to the metering chamber during a fill cycle.

According to another preferred method, the aerosol generator includes a reservoir containing at least 10 doses of a medicated fluid, the method further comprising filling a metering chamber with a predetermined volume of the medicated fluid and delivering the predetermined volume of the medicated fluid to the capillary passage. The method can include moving a displacement piston from a first position at which the metering chamber is filled with fluid to a second position at which the displacement piston deflects an elastomeric wall of the metering chamber. Control circuitry can be used to control a temperature of fluid in the capillary passage by pulsing power to the heater to heat the capillary passage as the fluid passes through the capillary passage, the fluid being volatilized and forming the aerosol within the mouthpiece. Preferably, the interior of the mouthpiece is supplied air only through the air passage, the air passage being opened and closed by a valve, the valve being closed during sensing of the pressure drop and the valve being opened within a predetermined period after sensing a predetermined pressure drop after which the aerosol is supplied to the interior of the mouthpiece.

DETAILED DESCRIPTION OF PREFERRED EMBODIMENTS OF THE INVENTION

As an overview, the present invention provides an aerosol generator such as a hand-held inhaler and method of delivering aerosol to a user inhaling on an outlet of a mouthpiece when a pressure drop is detected within the mouthpiece. A medicated fluid passing through a capillary passage is heated sufficiently to vaporize the fluid and form the aerosol by condensation of the vaporized fluid as it admixes with air. Air is supplied to the mouthpiece through an air passage which is initially closed during detection of the pressure drop. A metering chamber allows consistent delivery of precise doses of fluid to the capillary passage. The pressure drop is detected before air is supplied to the mouthpiece with the result that the aerosol can be delivered quickly to the user as the user begins to inhale on the mouthpiece. The quick delivery of aerosol provides more efficient use of the user's lung capacity.

An aerosol generator in accordance with a preferred embodiment of the present invention includes a housing, a pressure transducer and a fluid and air delivery system capable of delivering controlled amounts of a drug formulation to a user. During use of the aerosol generator, a user moves a sliding cap of the housing, thereby activating a master switch which places the aerosol generator in a ready to use condition. After activation of the master switch, when a user inhales on a mouthpiece of the aerosol generator, a pressure sensor senses a pressure drop in the mouthpiece. The pressure transducer sends a signal to a controller which activates a stepper motor to rotate a camshaft coupled with an inlet valve, a metering chamber, a dispensing piston, an outlet valve, and an air passage valve. As the camshaft rotates, fluid travels from the metering chamber to a heated capillary passage wherein the fluid is volatilized. After the volatilized fluid exits the capillary passage into the interior of the mouthpiece, ambient air mixes with the volatilized fluid, thereby providing an aerosol.

Figure 1:
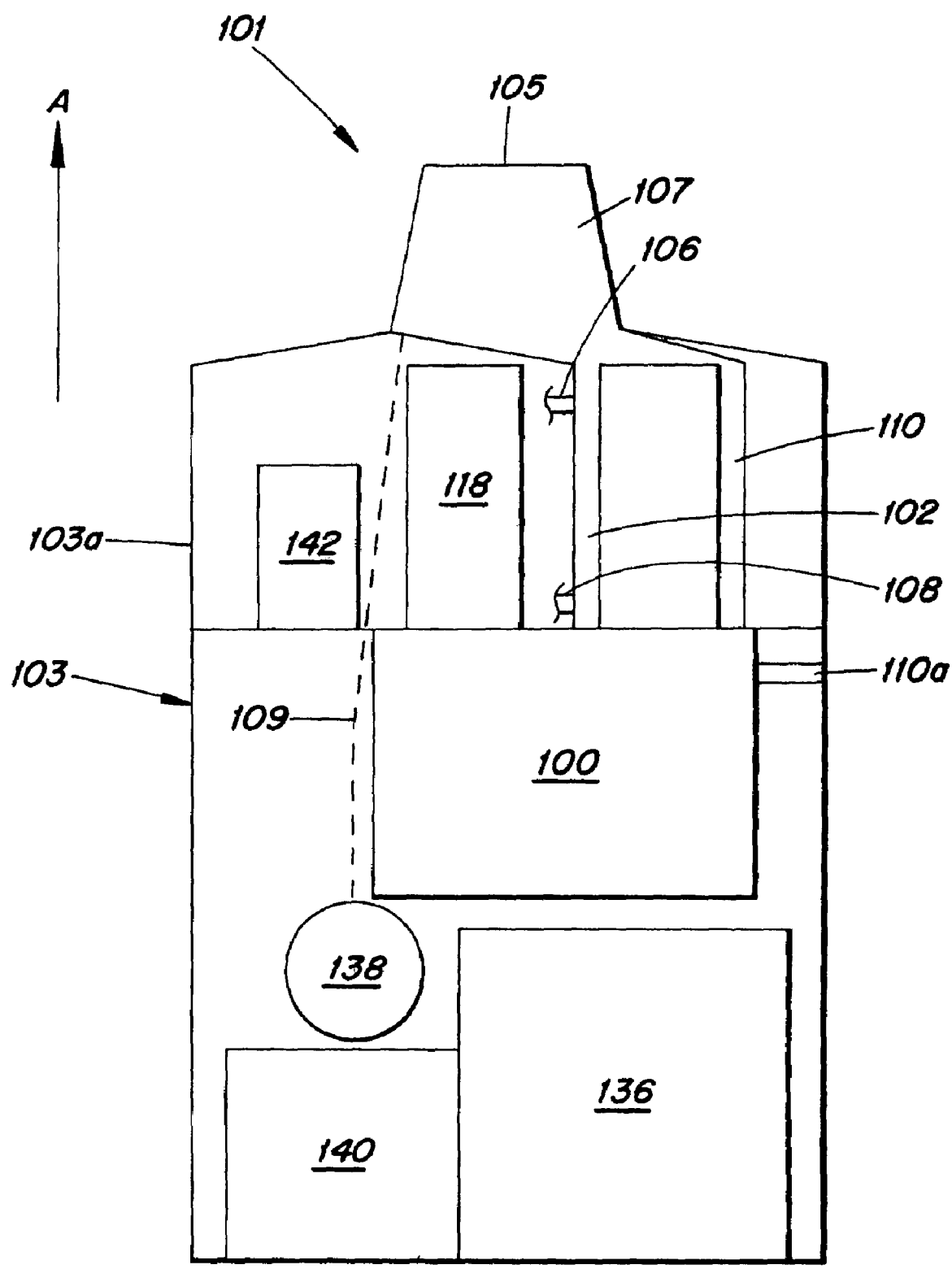
FIG. 1 is a schematic view of an aerosol generator in accordance with an embodiment of the present invention.

FIG. 1 illustrates a schematic view of an aerosol generator 101 in accordance with the preferred embodiment of the present invention. The aerosol generator 101 includes a housing 103, a capillary passage 102, a fluid and air delivery system 100 and a reservoir 118. Additionally, the aerosol generator 101 includes a master on/off switch 142, a pressure transducer 138, a battery pack 140 and control circuitry 136. The housing 103 includes a sliding cap 103a which operatively couples with the aerosol generator 101 such that during use of the aerosol generator 101, a user may move the cap 103a in an upward direction as indicated by directional arrow A. In one embodiment of the present invention, the housing 103 and cap 103a may be fabricated using plastic injection molding.

The capillary passage 102 of the aerosol generator 101 can comprise a piece of metal tubing through which an electrical current is passed via first electrode 106 and second electrode 108. However, the flow passage can be provided in other arrangements such as a channel in a polymer, glass, metal and/or ceramic laminate having a heater in the form of a layer of resistance heating material. The passage 102 can have a maximum width of 0.01 to 10 mm, preferably 0.05 to 1 mm, more preferably 0.1 to 0.5 mm. Alternatively, the capillary passage can be defined by transverse cross section area of the passage which can be $8 \times 10^{-5}$ to 80 mm$^2$, preferably $2 \times 10^{-3}$ to $8 \times 10^{-1}$ m$^2$ and more preferably $8 \times 10^{-3}$ to $2 \times 10^{-1}$ mm$^2$. With such an arrangement, the capillary passage 102 can heat medicament 112 (shown with reference to FIG. 2) from the reservoir 118 during use of the aerosol generator 101. In accordance with an embodiment of the present invention, the reservoir 118 has a dose capacity for delivering 5 μl doses preferably in a range between about 10 doses to about 500 doses, e.g., 50 to 250 doses. However, the dose capacity will depend on the desired dose volume and the desired dose can be preset depending upon the application of the aerosol generator. Also, the reservoir 118 may be designed as a removable part so as to be interchanged with a replacement reservoir during use of the aerosol generator 101. As such, the lifetime of the aerosol generator 101 may be increased due to the replaceability of the reservoir 118 and the medicament 112 disposed therein.

The aerosol generator 101 also includes the pressure transducer 138 in communication with the mouthpiece 105 via a passageway 109. A user activates the aerosol generator 101 by inhaling on an outlet of the mouthpiece 105. Upon inhalation, the change in pressure caused by inhalation activates the pressure transducer 138. The pressure transducer 138 senses the pressure change via the passageway 109, thereby activating the fluid and air delivery system 100. As will be discussed further on, the fluid and air delivery system 100 facilitates movement of the medicament 112 into the capillary passage 102.

In addition, the fluid and air delivery system 100 allows passage of ambient air into a condensation region 107 for admixture with vaporized medicament from the capillary passage 102 for drug formulation. The aerosol generator 101 includes an ambient air passage 110a which allows the passage of ambient air into the aerosol generator 101. The ambient air passage 110a feeds into an air passage 110 which allows for admixture of the ambient air in the condensation region 107 with vaporized medicament exiting the capillary passage 102. It should be noted that in an alternative embodiment of the present invention, a pressurized air source may be used to provide dilution air to mix with the vaporized material, such as a compressed air source physically located within the aerosol generator (not shown), a fan/blower to flow air into the mouthpiece, or the like.

In addition to the ambient air passage 110a, the aerosol generator 101 also includes the control circuitry 136. As will be discussed further on with reference to FIG. 5, the control circuitry 136 controls the temperature of the capillary passage 102 during operation of the aerosol generator 101. The control circuitry 136 can also monitor a LCD used to display remaining doses, control a stepper motor 134 (shown with reference to FIG. 2) of the fluid and air delivery system 100 during operation of the aerosol generator 101, monitor an optical sensor which cooperates with the stepper motor to ensure accurate positioning of the motor, monitor the initial pressure drop, monitor the condition of the battery 140, monitor the operation of the heated capillary 102, and the like.

The aerosol generator 101 also includes the battery pack 140. In the embodiment shown with respect to FIG. 1, the battery pack 140 may be a rechargeable 6 V nickel metal hydride (NiMH) battery using five cells. In this embodiment, the battery pack 140 may use five Sanyo HF-C1U, 600 mAh NiMH batteries in series which allows for delivery of 100 doses of 5 μl volumes of medicament. The battery pack 140 provides a power source to components of the aerosol generator 101 (e.g., control circuitry 136, pressure transducer 138, etc.) and the master on/off switch 142.

The master on/off switch 142 controls powering up and powering down of the aerosol generator 101 during operation. Moreover, the master on/off switch 142 activates an LCD (not shown), which in one embodiment of the present invention, provides information such as the amount of doses left within the reservoir 118, whether or not failure of the heater has occurred, whether a low voltage of the battery pack 140 is detected, and the like.

During operation of the aerosol generator 101, a user moves the cap 103a to an open position in the direction A to activate components of the aerosol generator. With the cap 103a in the open position, the user inhales on the mouthpiece 105. Inhalation by the user on the mouthpiece 105 provides a pressure drop in the interior of the mouthpiece which is detected by the pressure transducer 138. Upon sensing the pressure drop, the pressure transducer 138 sends a signal to a controller which operates the fluid and air delivery system 100 as more clearly shown with reference to FIG. 2.

Figure 2:
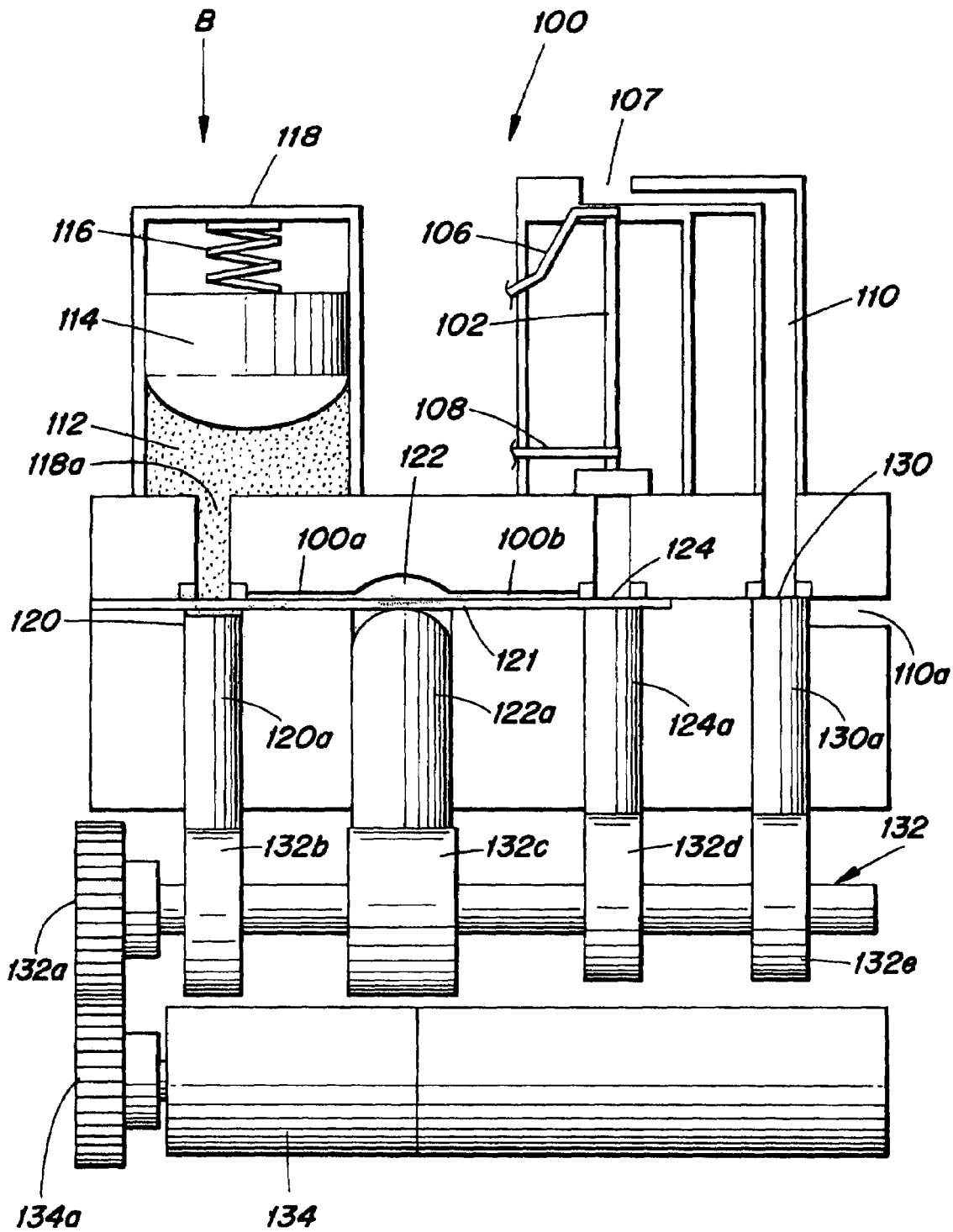
FIG. 2 is a schematic view of the fluid and air delivery system shown with reference to FIG. 1 in accordance with an embodiment of the present invention.

FIG. 2 illustrates a schematic view of the fluid and air delivery system 100 shown with reference to FIG. 1 in accordance with an embodiment of the present invention. The fluid and air delivery system 100 includes the aforementioned capillary passage 102, the first and second electrodes 106 and 108, and the reservoir 118. The reservoir 118 includes a compression spring 116, a plunger 114 and the medicament 112. The compression spring 116 provides pressure on the plunger 114 in a direction indicated by a directional arrow B to maintain flow of liquid medicament 112 through passage 118a and into metering chamber 122 when inlet valve 120 is open.

The inlet valve 120 forms a portion of the fluid and air delivery system 100 of the aerosol generator 101. In an embodiment of the present invention, the fluid and air delivery system 100 includes various valves actuated by camshaft 132 having cam lobes and an engagement gear 132a.

The engagement gear 132a couples with an engagement gear 134a of stepper motor 134. As such, when the stepper motor 134 rotates, the camshaft 132 also rotates, via the engagement gears 134a and 132a. As the camshaft 132 rotates, camshaft lobes 132b through 132e also rotate. During rotation of the camshaft 132, the camshaft lobes 132b through 132e operatively couple with valve plungers 120a, 124a and 130a and dispensing plunger 122a which are biased via springs (not shown) so as to press against the camshaft lobes. During rotation, the camshaft lobes 132b through 132e activate the valve plungers 120a, 124a, 130a and dispensing plunger 122a in a desired sequence determined by the configuration of the camshaft lobes. For example, the camshaft lobe 132b operatively couples with the plunger 120a, thereby opening and closing the valve 120 during rotation of the camshaft. The camshaft lobe 132c operatively couples with the dispensing plunger 122a in order to empty the metering chamber 122 during rotation of the camshaft. Preferably, the dispensing plunger ejects fluid out of the metering chamber 122 at a substantially constant flow rate. The camshaft lobe 132d operatively couples with the plunger 124a, thereby opening and closing the valve 124, while the camshaft lobe 132e operatively couples with the plunger 130a, which opens and closes the valve 130 during rotation of the camshaft.

As previously discussed, when the cap 103a is in the open position and a user inhales on the mouthpiece 105, the pressure drop in the mouthpiece 105 is sensed by the pressure transducer 138. Upon detection of the pressure drop by the transducer 138, the pressure transducer 138 sends a signal to the control circuitry 136 which in turn causes activation of the stepper motor 134. In an embodiment of the present invention, the stepper motor 134 may be any stepper motor capable of controllably driving the camshaft 132 a precise amount (e.g., one revolution). In this embodiment, the stepper motor may be of the type that can be obtained from MicroMo Electronics, Inc. located in Clearwater, Fla.

The metering chamber 122 can be emptied by moving the dispensing plunger 122a. For instance, when the camshaft lobe 132c engages with the dispensing plunger 122a, an end of the dispensing plunger 122a presses against an elastomeric wall of the metering chamber 122 until the elastomeric wall is pressed against an opposing wall of the chamber. As a result, fluid in the chamber is forced into passage 100b while fluid in passage 100b is forced into the capillary passage. The elastomeric wall preferably forms a seal over the passages 100a, 110b, the inlet valve 120 and outlet valve 124 such that the inlet and outlet valves can be opened or closed when the plunger 120a, 124a presses the elastomeric wall against a valve seat around the valve opening. The metering chamber 122 ensures that a desired amount of the medicament 112 is delivered by the aerosol generator 101 to a patient. In this embodiment of the present invention, the metering chamber has a predetermined volume (e.g., 5 μl). Nonetheless, it is to be understood that the metering chamber 122 can be designed with any desired volume depending upon the application of the aerosol generator 101. After delivery of the predetermined volume of medicament to the capillary passage 102, valve 124 is closed by engagement of lobe 132d with plunger 124a.

The camshaft 132 also includes the camshaft lobe 132e which operatively couples with the plunger 130a. The plunger 130a is operatively associated with an air valve 130 such that upon movement of the plunger 130a via rotation of the camshaft lobe 132e, the air valve 130 opens. The air valve 130 allows the admittance of ambient air into the aerosol generator 101 via the ambient air passage 110a. The air valve 130 couples the ambient air passage 110a with the air passage 110 such that upon opening by the valve 130, ambient air entering the ambient air passage 110a continues through the air passage 110 for admixture with vaporized medicament exiting the capillary passage 102 within the condensation space 107 (shown with reference to FIG. 1). The air valve 130 could also be used to admit pressurized air rather than ambient air.

FIG. 2 illustrates the condition of the fluid and air delivery system 100 during a fill cycle wherein the metering chamber is filled with fluid. During a fill cycle, camshaft 132 has rotated such that the camshaft lobe 132b opens valve 120 and camshaft lobe 132d closes valve 124 while maintaining the dispensing plunger 122a in a position which allows the medicament 112 to fill the metering chamber 122.

Figure 3:
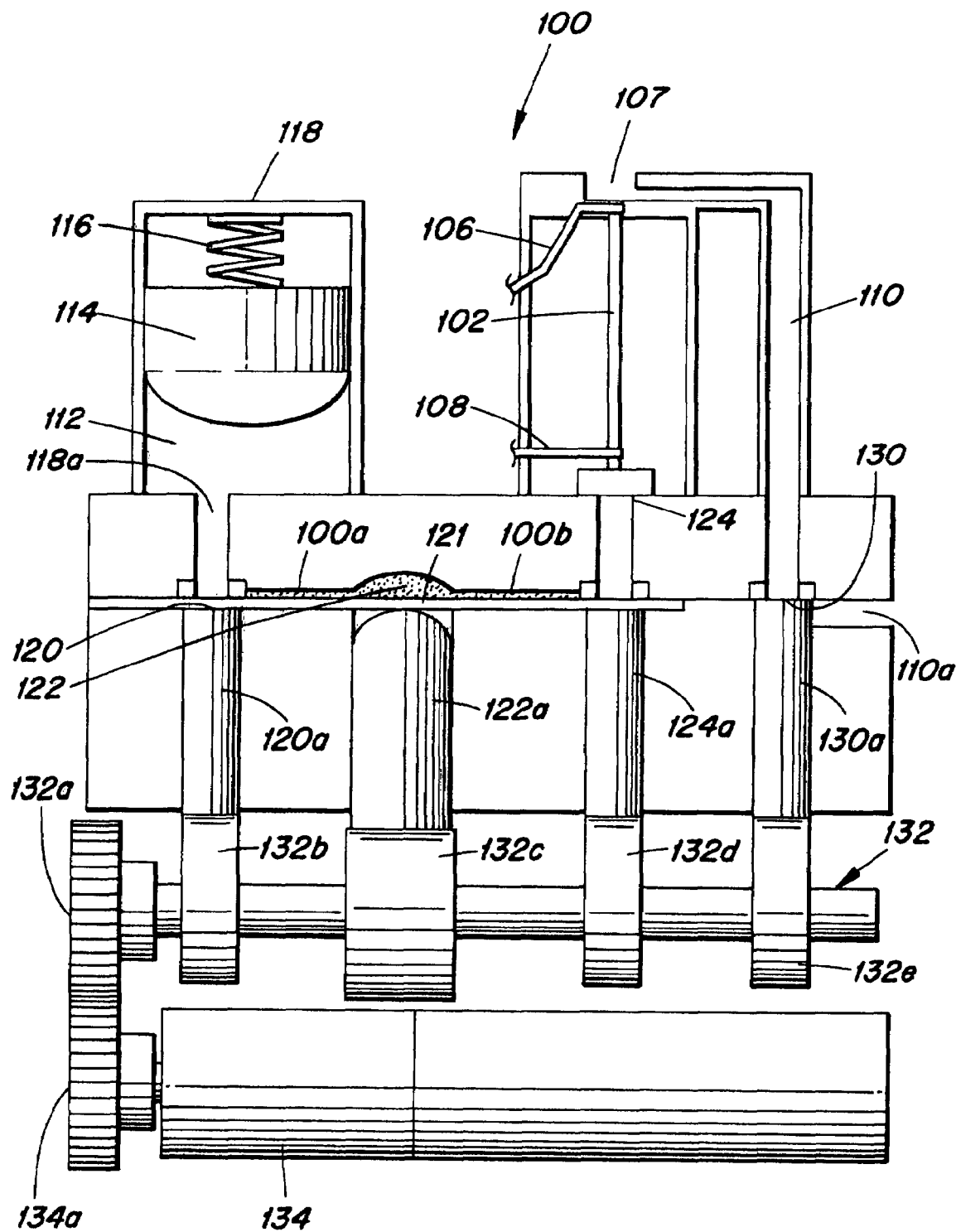
FIG. 3 is a schematic view of the fluid and air delivery system shown with reference to FIG. 2 wherein the fluid and air delivery system is in a reservoir closure operation.

FIG. 3 is a schematic view of the fluid and air delivery system 100 wherein the fluid and air delivery system 100 is at the beginning of an aerosol delivery cycle. During this operation, the camshaft lobe 132b closes the valve 120. As valve 120 closes, the camshaft lobes 132d and 132e maintain the valves 124 and 130 in a closed position while the camshaft lobe 132c maintains the dispensing plunger 122a in a non-dispensing position.

Figure 4:
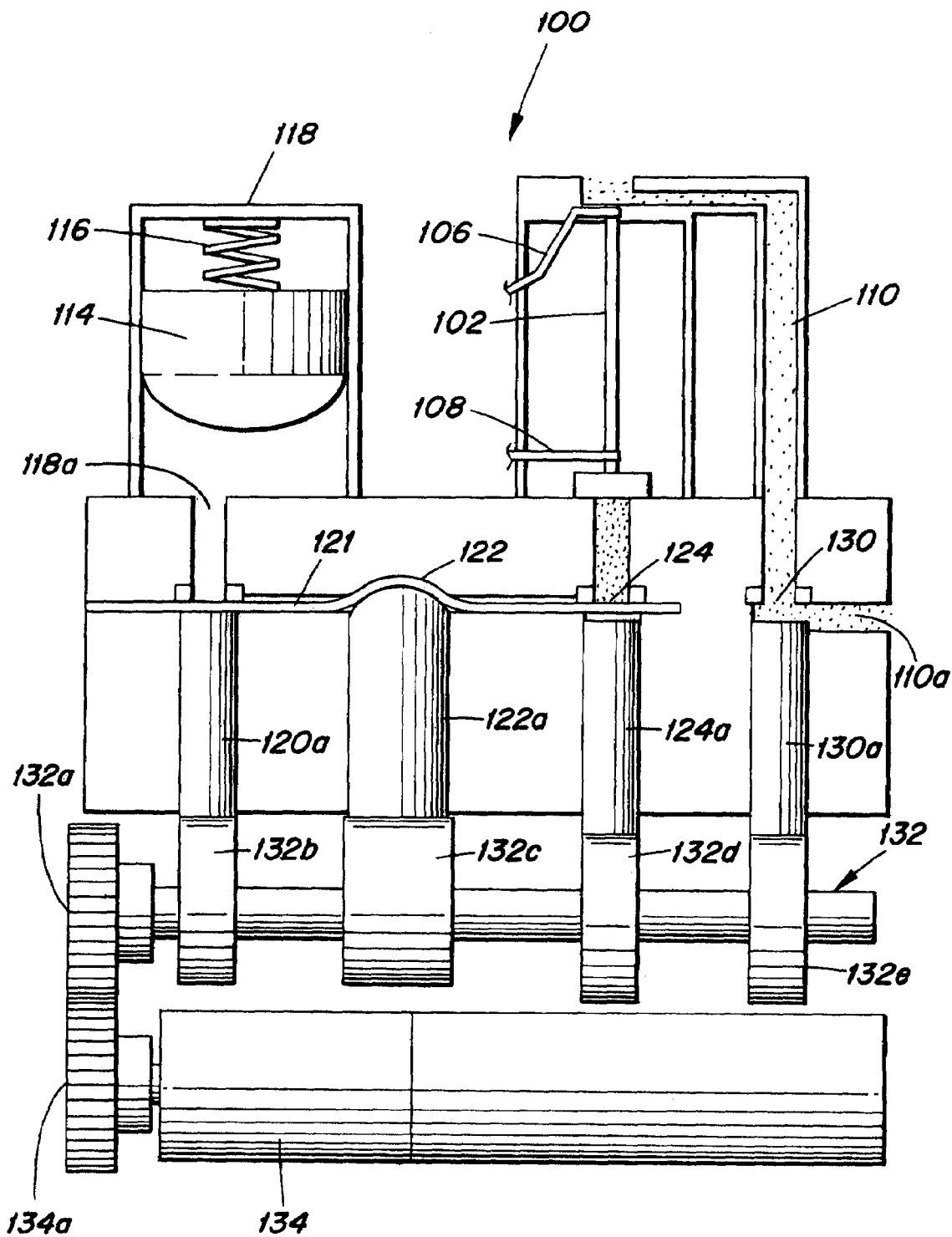
FIG. 4 is a schematic view of the fluid and air delivery system shown with respect to FIG. 3 wherein the fluid and air delivery system is in a dispensing cycle in accordance with an embodiment of the present invention.

FIG. 4 is a schematic view of the fluid and air delivery system 100 wherein the fluid and air delivery system 100 is at the end of the aerosol delivery cycle. During the aerosol delivery cycle, the camshaft lobe 132c moves the dispensing plunger 122a into a dispensing position wherein the hemispherical plunger head presses an elastomeric wall of the metering chamber towards an opposed wall to thereby empty the hemispherical metering chamber 122. As the dispensing plunger 122*a* begins to press against the elastomeric wall, lobes 132*d* and 132*e* move the plungers 124*a* and 130*a* into open positions to thereby open valves 124 and 130.

As the medicament 112 flows into the heated capillary passage 102 and exits as a vaporized fluid, ambient air travels from the ambient air passage 110*a* into the air passage 110 due to the inhalation of the user. By maintaining the air valve 130 closed until aerosol is generated in the mouthpiece, aerosol can be supplied to the patient early in the patient's inhalation breath cycle to thereby deliver a precise dose of medication to the lungs of the patient.

Figure 5:
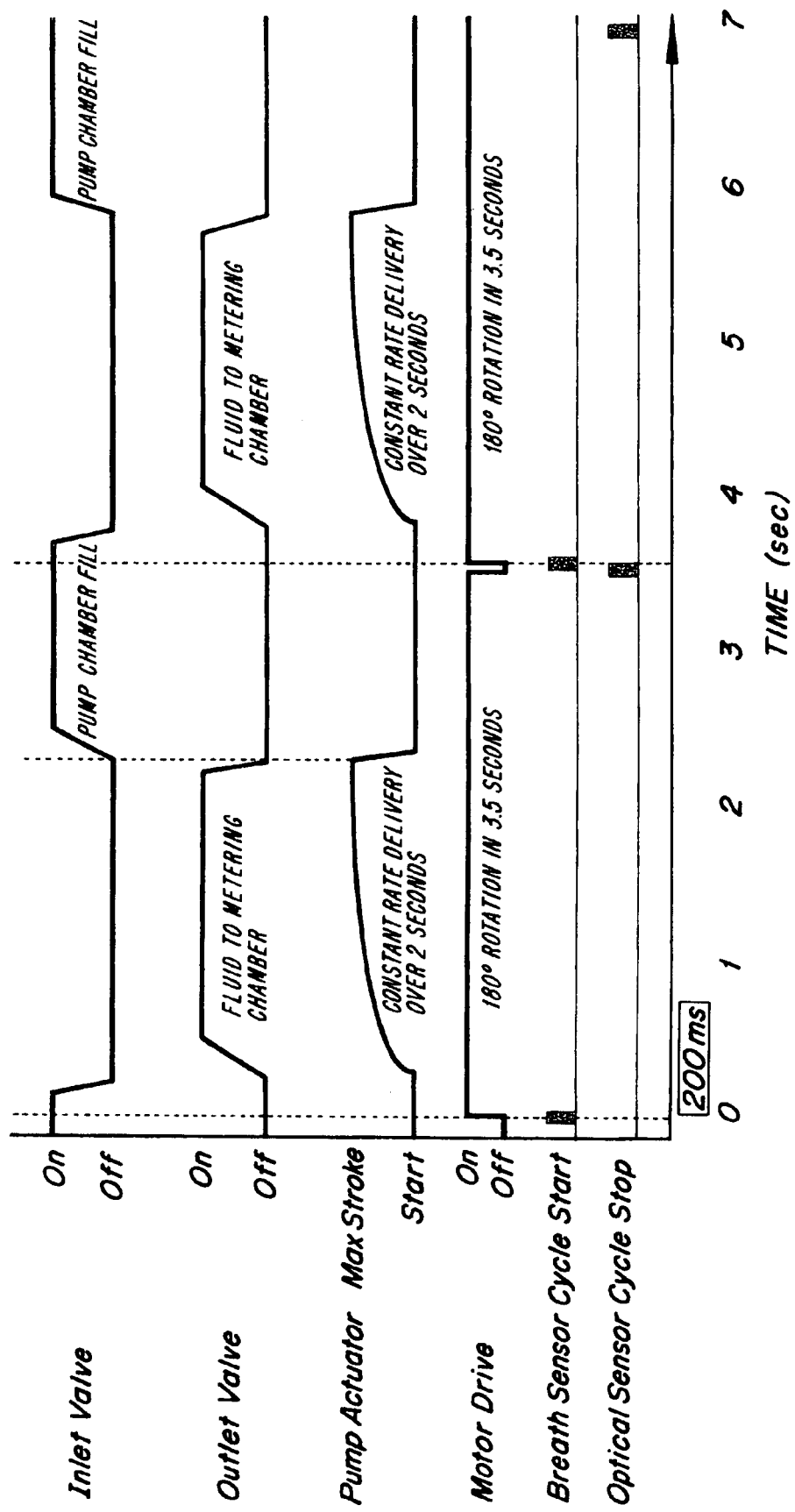
FIG. 5 is a schematic of a timed sequence of operation of the aerosol generator in accordance with a preferred embodiment of the invention.

FIG. 5 illustrates a time sequence of the inlet valve, the outlet valve, the pump actuator (dispensing plunger), the stepper motor, the breath activation sensor and the optical sensor coupled to the stepper motor. As shown, within 200 ms of detecting a user drawing on the mouthpiece, the inlet valve is closed after which the outlet valve is opened. At the same time, the air passage valve is opened to allow ambient air to be drawn into the mouthpiece by the patient inhaling through the outlet of the mouthpiece. With the outlet valve open, the pump actuator (dispensing plunger) provides a constant rate of delivery of a precise volume of fluid to the heated capillary passage over a 2 second period. The ambient air admixes with the vaporized fluid delivered by the heated capillary passage to form an aerosol and the patient inhales the aerosol. Subsequently, the outlet valve is closed and then the inlet valve is opened to refill the metering chamber. Because the aerosol is delivered at the beginning of the patient's breath inhalation, the drug formulation in the aerosol can be effectively administered.

Figure 6:
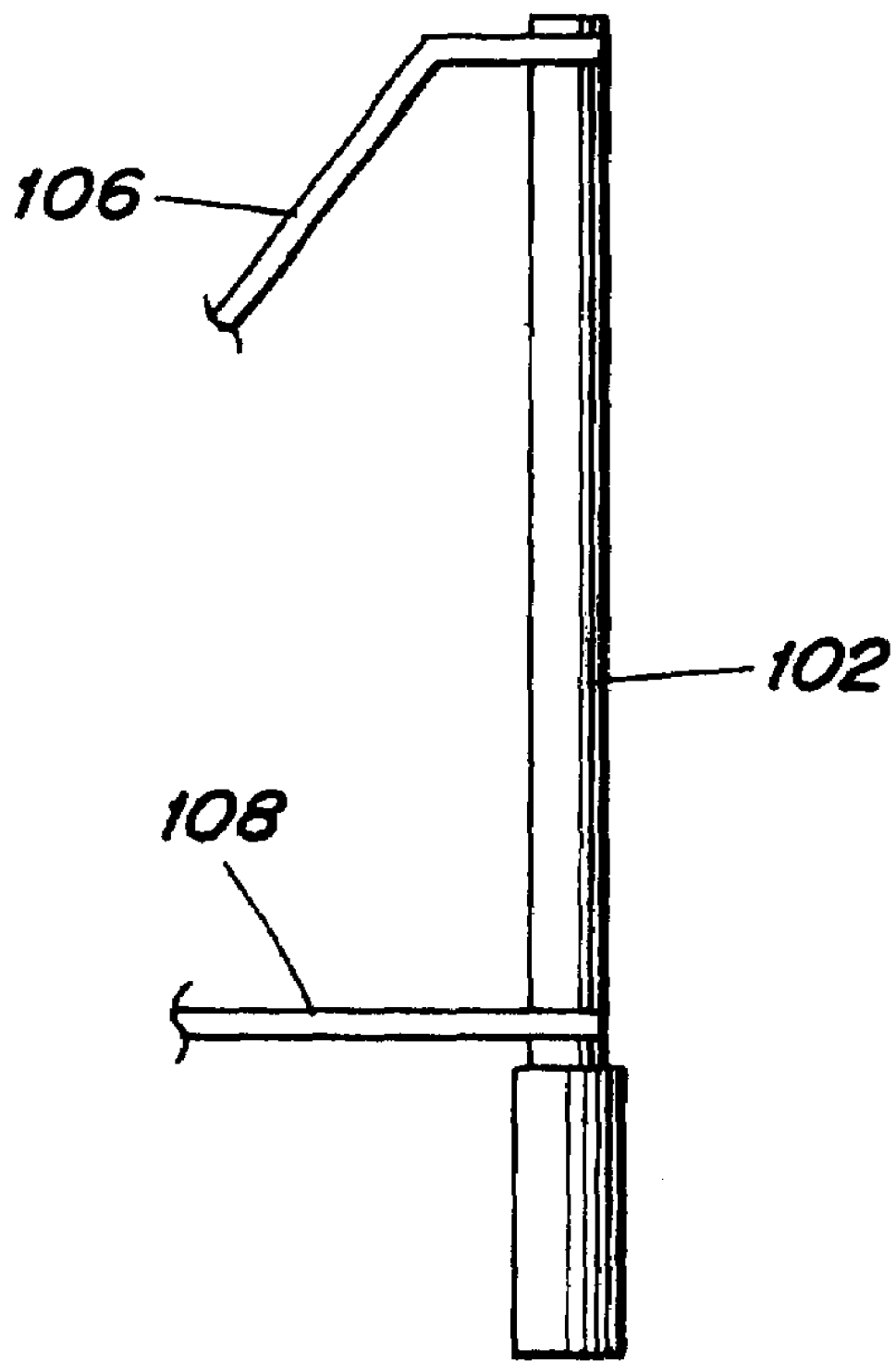
FIG. 6 is an embodiment of the present invention illustrating a schematic view of the capillary with a first electrode and a second electrode.

FIG. 6 is an embodiment of a preferred heater arrangement in which the capillary passage comprises an electrically conductive tube provided with the first electrode 106, which is the downstream electrode, and the second electrode 108, which is the upstream electrode. In this embodiment, the capillary passage 102 is a controlled temperature profile design such as disclosed in copending and commonly assigned application Ser. No. 09/957,026, filed Sep. 21, 2001, which is incorporated herein by reference. In the controlled temperature profile capillary, the downstream electrode has an electrical resistance sufficient to cause heating of the electrode during use of the device, thereby minimizing heat loss at the outlet end of the capillary tube.

According to one aspect of the present invention, the capillary passage is formed from a tube made entirely of stainless steel or other electrically conductive materials, or a non-conductive or semi-conductive tube incorporating a heater formed from an electrically conductive material such as platinum (Pt). Two electrodes are connected at spaced positions along the length of the tube such that a heated section is defined between the two electrodes. A voltage applied between the two electrodes generates heat in the heated section based on the resistivity of the stainless steel or other material making up the tube or heater, and other parameters such as the cross-sectional area and length of the heated section. As the fluid flows through the capillary tube into the heated section between the first and second electrodes, the fluid is heated and converted to a vapor. The vapor passes from the heated section of the capillary tube to the tip of the capillary tube and exits from the outlet end of the capillary tube. If the volatilized fluid enters ambient air from the tip of the capillary tube, the volatilized fluid condenses into small droplets, thereby forming an aerosol preferably having a desired droplet size, preferably 0.5 to 2.5 μm.

The temperature of the liquid in the capillary flow passage can be calculated based on the measured or calculated resistance of the heating element. In a preferred embodiment, the heater is a portion of a metal tube or a heater can be a strip or coil of resistance heating material. The controller preferably regulates the temperature of the flow passage by monitoring the resistance of the heater.

Resistance control can be based on a simple principle: The resistance of the heater increases as its temperature increases. As power is applied to the heating element, its temperature increases because of resistive heating and the actual resistance of the heater also increases. When the power is turned off, the temperature of the heater decreases and correspondingly its resistance decreases. Thus, by monitoring a parameter of the heater (e.g., voltage across the heater using known current to calculate resistance) and controlling application of power, the controller can maintain the heater at a temperature which corresponds to a specified resistance target. The use of one or more resistive elements could also be used to monitor temperature of the heated liquid in cases where a resistance heater is not used to heat the liquid in the flow passage.

The resistance target is selected to correspond to a temperature that is sufficient to induce a heat transfer to the liquid material such that liquid is volatilized and expands out the open end of the capillary. The controller effects closing of the switch which activates the heating thereby applying for a duration of time, energy to the heater and after and/or during such duration, determines the real time resistance of the heater, using input from the measuring device. In the preferred embodiment, the resistance of the heater is calculated by measuring the voltage across a shunt resistor (not shown) in series with the heater (to thereby determine current flowing to the heater) and measuring the voltage drop across the heater (to thereby determine resistance based on the measured voltage and current flowing through the shunt resistor). To obtain continuous measurement, a small amount of current can be continually passed through the shunt resistor and heater for purposes of making the resistance calculation and pulses of higher current can be used to effect heating of the heater to the desired temperature.

If desired, the heater resistance can be derived from a measurement of current passing through the heater or other techniques can be used to obtain the same information. The controller, then makes decisions as to whether or not to send an additional duration of energy based on the difference between desired resistance target for the heater and the actual resistance as determined by the controller.

In a developmental model, the duration of power supplied to the heater was set at 1 msec. If the monitored resistance of the heater minus an adjustment value is less than the resistance target, the controller is programmed to supply another duration of energy by leaving the switch in the closed ("on") position. The adjustment value takes into account factors such as heat loss of the heater when not activated, the error of the measuring device and cyclic period of the controller and switching device, among other possibilities. In effect, since the resistance of the heater varies as a function of its temperature, resistance control can be used to achieve temperature control.

In accordance with an embodiment of the present invention, the capillary passage 102 uses 32 gauge SS304 tubing having a fluid heating section of 12 mm. In addition, in this embodiment, the downstream electrode 106 is a 3.5 mm length of 29 gauge tubing while the upstream electrode 108 may have any geometry which minimizes the resistance of the electrode 108, such as gold (Au) plated copper (Cu) pins.

The control circuitry 136 can control the temperature of the capillary passage 102 by monitoring the resistance of the heated tube capillary 102. In an embodiment of the present invention, a target temperature for the capillary passage 102 is preferably about 220° C. In this embodiment, a measured electrical resistance of the heated capillary tube 102 is preferably 0.4 ohms for a target temperature of about 220° C. In order to achieve a resistance of 0.4 ohms, the control circuitry 136 pulses power to first electrode 106. In an embodiment of the present invention, the control circuitry 136 measures voltage and current in order to calculate the resistance across a length of the capillary tube 102. If the control circuitry 136 calculates that the resultant resistance is below the target value, the control circuitry 136 turns power on for 10 milliseconds. The control circuitry 136 continues to repeat this process until the target resistance for the capillary tube 102 is achieved. Likewise, if the control circuitry 136 measures the resistance higher than required for the temperature of the capillary passage 102, the control circuitry 136 turns off power for 10 milliseconds. In this embodiment, the control circuitry 136 may include any processor capable of controlling the resistance of the capillary tube 102 via the electrodes 106 and 108, such as a microchip PIC16F877, available from Microchip Technology Inc., located in Chandler, Ariz., which is programmed in assembly language. It should also be noted that the control circuitry 136 includes functionality for controlling both the stepper motor 134 and optical and pressure sensors, checking the status of both the battery pack 140 and the LCD incorporated into the master on/off switch 142. The control circuitry 136 can also include functionality via the processor for displaying the number of remaining doses, information on patient compliance, lockout times and/or child safety locks. After vaporization of the medicament 112 within the capillary passage 102, the vaporized medicament expands into the condensation region 107 for admixture with the ambient air for condensation.

The aerosol generator can produce condensation aerosols with high number concentrations and particle sizes in a range between about 0.5 µm and about 2.5 µm. The aerosol generator can be miniaturized to a hand-held, portable device with considerable potential for the targeted delivery of drugs to the deep lung. These aerosols offer a number of advantages for delivering drugs to the deep lung. For example, mouth and throat deposition are minimized while deposition in the deep lung is maximized, especially when combined with a breath hold. Moreover, when using an appropriate hydrophilic carrier, deposition may be further enhanced by hygroscopic growth.

The median particle size of the aerosol may be increased by increasing the capillary size and/or decreasing the fluid flow rate through the capillary passage. The aerosol generator preferably generates aerosols wherein 95% of the aerosol particles (aerosol droplets) are smaller than 5.6 µm and more preferably in a range of between about 0.5 µm to about 2.5 µm. The aerosol generator preferably incorporates a processor chip for controlling the generation process. The processor, with suitable sensors, also triggers the aerosol generation at any desired time during an inhalation. The processor may also store and report compliance information for patient feedback. During use of the aerosol generator, the drug to be aerosolized is dissolved in a carrier. By the appropriate choice of hydrophilic carriers, this aerosol generator can take advantage of hygroscopic growth in the respiratory system.

Operation of the preferred aerosol generator is as follows. First, a fluid carrier is pumped through the heated capillary passage along with a drug. The fluid vaporizes in the passage and exits as a vapor jet from the open end of the passage. The vapor jet entrains and mixes with ambient air, cools and then condenses to form a highly concentrated, fine aerosol. The heated passage can take a variety of forms, including the use of a glass capillary wrapped by a heater and a capillary formed from stainless steel. The application of heat to vaporize the aerosol liquid is usually accomplished by resistive heating from passing an electric current through the metal capillary. The applied power is adjusted to maximize the conversion of the fluid into an aerosol.

The aerosol generator can generate aerosols over a range of fluid flow rates dependent on the size of the capillary and the power available to vaporize the fluid. A fluid which may be used to generate aerosols is propylene glycol (PG) obtained as USP grade (CAS #57-55-6) from Fisher Scientific in Atlanta, Ga. The boiling point of PG is 189° C. and it has a density of 1.036 g/mL. Solute compounds used as models for drugs were triphenylmethane (CAS #519-73-3) and oleyl alcohol (CAS #143-28-2) also available from Fisher Scientific in Atlanta, Ga.

Figure 7:
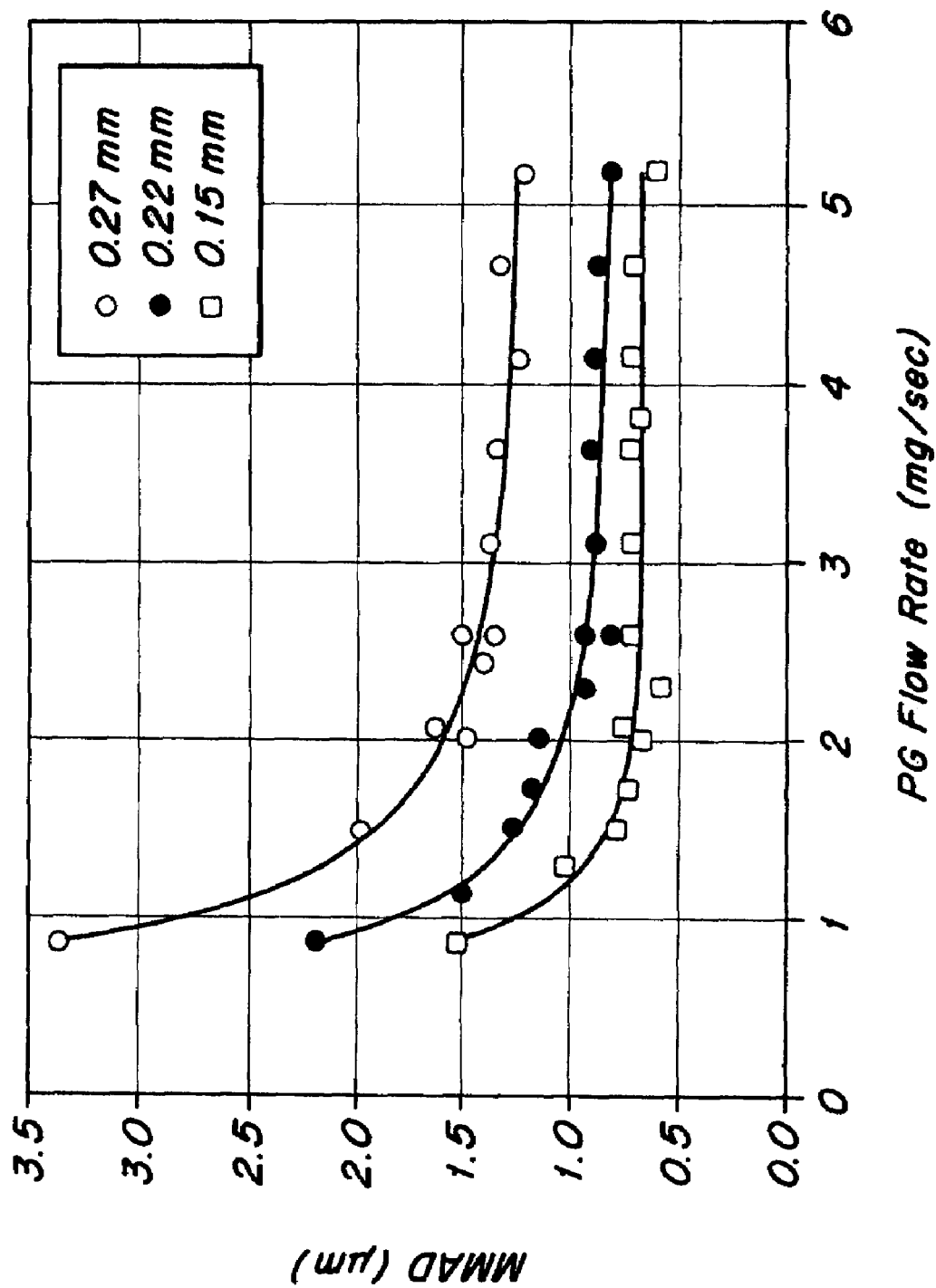
FIG. 7 is a graph illustrating the effect of a capillary diameter and a mass flow rate on a particle size for a propylene glycol aerosol in accordance with an embodiment of the present invention.

A mass median aerodynamic diameter (MMAD) of the aerosol produced by the aerosol generator is a function of the diameter of the heated capillary sized flow passage and the input flow rate. FIG. 7 presents exemplary MMAD plotted as a function of the PG flow rate for several capillary diameters. The data shown with reference to FIG. 7 reflects PG without solute. As the flow rate increases, the MMAD of the aerosol first decreases then levels off to a constant value. As the capillary diameter increases, the particle size for the entire flow rate range also increases. In an embodiment of the present invention, these two effects can be used to tailor the MMAD of the aerosol.

Figure 8:
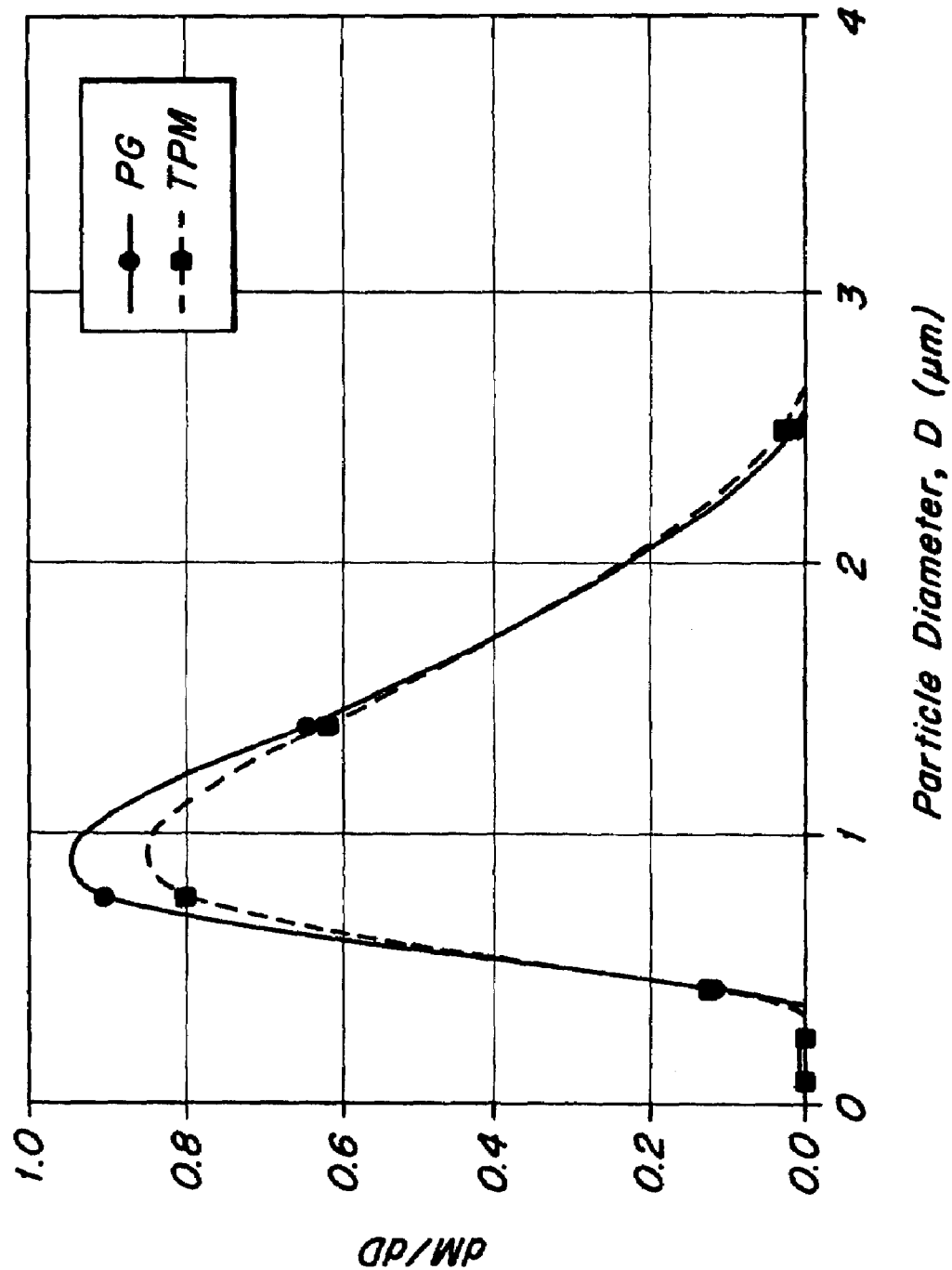
FIG. 8 is a graph illustrating a chemical distribution for propylene glycol and triphenylmethane as a function of particle size showing behavior when a solute and a liquid vehicle have equivalent vapor pressures.

Adding a solute, such as a drug, to the PG can change the condensation process since the solute may act as nucleating agent for the PG. If the solute has a vapor pressure similar to the PG, the solute condenses in the aerosol at the same time that the PG condenses. When triphenylmethane (TPM) has a concentration of 0.28% in PG, TPM behaves similarly to the PG and both the TPM and the PG form an aerosol in which the TPM has the same chemical distribution as the total aerosol, as more clearly shown with reference to FIG. 8. In the graph shown with reference to the FIG. 8, the fluid feed rate was 2.5 mg/sec and the PG had a MMAD between about 1.1 µm and 1.5 µm.

Figure 9:
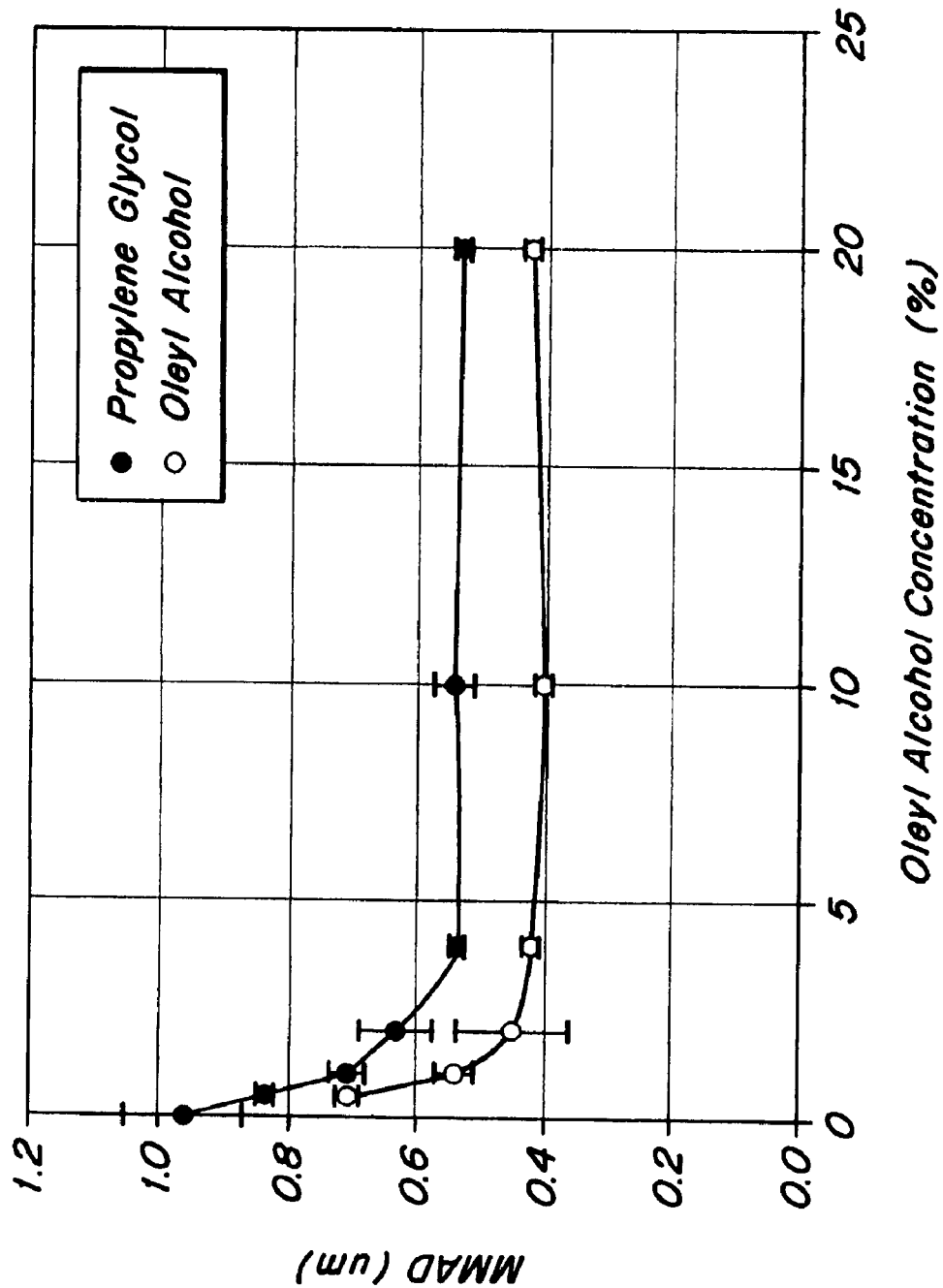
FIG. 9 is a graph showing the effect of oleyl alcohol concentration on MMAD showing behavior when a solute and liquid vehicle have dissimilar vapor pressures.

In an embodiment where the solute is less volatile than the PG, the solute may start the condensation process early and serve as a nucleating agent for subsequent PG condensation. In this embodiment, a difference between the chemical distribution of the solute and the mass distribution of the overall aerosol may occur. This manifests itself in different MMADs for the solute and the PG. It should be noted that these are not two separate aerosols. Instead, one aerosol is produced having a varying chemical composition as a function of size. The MMADs can be a function of the solute concentration as more clearly shown with reference to FIG. 9 for oleyl alcohol (OA) in PG due to the solute effects on the nucleation of the PG aerosol. In the embodiment shown with reference to FIG. 9, the fluid feed rate was 3.3 mg/sec. It should be noted that the presence of a solute which acts as a nucleating agent for PG causes a decrease in the MMAD of the aerosol. In this embodiment, total recovery in a cascade impactor and USP induction port for OA having a 10% by weight solution was 95.1±1.2% of the amount pumped into the capillary.

As may be appreciated, a preferred embodiment of the present invention provides an aerosol generator capable of controlled vaporization and condensation of a drug formulation. Additionally, a preferred embodiment of the present invention provides a replaceable reservoir having a predetermined amount of doses of medicament. A preferred embodiment of the aerosol generator can provide immediate delivery of aerosol to a patient so as not to waste lung capacity which may be limited due to the health of the patient. Also, a preferred embodiment of the aerosol generator can provide consistent delivery of controlled amounts of drug formulation to a patient. As such, overall costs associated with a preferred embodiment of the aerosol generator are reduced since the user may continually replace the reservoir and the batteries, thereby increasing the longevity of the aerosol generator.

The above are exemplary modes of carrying out the invention and are not intended to be limiting. It will be apparent to those of ordinary skill in the art that modifications thereto can be made without departure from the spirit and scope of the invention as set forth in the accompanying claims. For instance, while a heated capillary has been described as the preferred aerosol generator, the aerosol can be generated by other techniques such as by propellant-based aerosol generators or nebulizer-based aerosol generators wherein liquid or powder can be formed into an aerosol by pressurized gas or via ultrasonic vibration. Further, while a heated capillary tube has been described as the preferred heated capillary passage, the capillary passage can be provided as one or more channels in a laminate having a heater arranged along the channel(s), multiple capillary tube arrangements, a passage having a heater located inside the passage, coaxial arrangements wherein the fluid flows through an annular channel or the like. Further, while a cammed arrangement has been described as the preferred valve operating mechanism, individual solenoid valves or other valve actuating arrangement can also be used in place thereof.

What is claimed is:

1. An aerosol generator comprising:
a mouthpiece having an outlet through which aerosol is supplied to a user of the aerosol generator;
an air passage through which air is supplied to an interior of the mouthpiece;
a sensor detecting a pressure drop in the interior of the mouthpiece;
a housing;
a capillary passage disposed within the housing;
a heater disposed within the housing;
a reservoir disposed within the housing;
a metering chamber disposed within the housing, the metering chamber being supplied fluid from the reservoir by a first flow passage and the capillary passage being supplied fluid from the metering chamber by a second flow passage;
a power source adapted to supply electrical power to the heater;
a first valve adapted to open and close the first flow passage;
a second valve adapted to open and close the second flow passage;
a third valve adapted to open and close the air passage; and
a motor and a camshaft, the camshaft including a plurality of camshaft lobes operatively associated with the first, second and third valves, the camshaft lobes being operable to close the first valve and open the second and third valves during an aerosol delivery cycle in which fluid is supplied to the capillary passage.

2. The aerosol generator as recited in claim 1, wherein the camshaft lobes are operable to open the first valve and close the second and third valves during a fill cycle in which fluid is supplied to the metering chamber.

3. The aerosol generator as recited in claim 1, the aerosol generator further comprising:

a stepper motor operatively coupled with the camshaft wherein the stepper motor rotates the camshaft to open and close the first, second and third valves.

4. The aerosol generator as recited in claim 1, wherein the reservoir is removably attached to the housing, the reservoir including a piston operable to pressurize fluid in the reservoir.

5. The aerosol generator as recited in claim 1, wherein the housing includes a cap slidably attached to the housing, the cap including the mouthpiece at one end thereof and the cap being slidable from a first storage position to an aerosol delivery position at which the aerosol generator is in a breath actuation mode wherein the user can obtain a dose of aerosol by inhaling on the outlet.

6. The aerosol generator as recited in claim 5, wherein the aerosol generator further comprises;
a liquid crystal display located on a portion of the housing which is exposed when the cap is moved to the aerosol delivery position.

7. The aerosol generator as recited in claim 1, further comprising a controller, the sensor being operable to send the controller a signal when the user inhales on the outlet of the mouthpiece.

8. The aerosol generator as recited in claim 7, wherein the sensor comprises a transducer which detects a pressure drop in the interior of the mouthpiece when the user inhales on the outlet of the mouthpiece.

9. The aerosol generator as recited in claim 1, further comprising a dispensing piston which engages an elastomeric wall of the metering chamber during the aerosol delivery cycle.

10. The aerosol generator as recited in claim 1, further comprising a dispensing piston which engages an elastomeric wall of the metering chamber during the aerosol delivery cycle, the camshaft including a camshaft lobe operable to reciprocate the dispensing piston.

11. The aerosol generator as recited in claim 1, further comprising a controller adapted to monitor a parameter of the heater and deliver power from the power supply to the heater such that the heater is maintained at a desirable temperature range during the aerosol delivery cycle.

12. The aerosol generator as recited in claim 1, wherein the aerosol generator is a hand-held inhaler, the interior of the mouthpiece is supplied air only through the air passage, and the aerosol generator includes a valve control mechanism which opens the third valve within a predetermined time period after the sensor detects a pressure drop in the interior of the mouthpiece as the user inhales on the outlet.

13. The aerosol generator as recited in claim 1, wherein the motor driven camshaft is operable to open and close the first, second and third valves according to a programmed cycle upon one rotation of the camshaft, the aerosol generator including a light sensor operable to sense when the camshaft completes a single revolution.

14. A method for generating an aerosol with an aerosol generator according to claim 1, the method comprising:
sensing a pressure drop in an interior of the mouthpiece with the sensor when the user inhales on the outlet of the mouthpiece;
supplying aerosol to the interior of the mouthpiece when the pressure drop is detected; and
supplying air to the interior of the mouthpiece by opening the air passage when the pressure drop is detected.

15. The method for generating an aerosol as recited in claim 14, wherein the aerosol generator comprises a slidable cap, the method further comprising:

sliding the cap from a closed position to an open position, the open position activating components of the aerosol generator to deliver aerosol to the user when the pressure drop is detected.

16. The method for generating an aerosol as recited in claim 14, wherein the heater heating the capillary passage sufficiently to volatilize fluid therein, the volatilized fluid admixing with air and forming the aerosol.

17. The method for generating an aerosol as recited in claim 16, wherein the aerosol generator includes control circuitry which controls a temperature of fluid in the capillary passage by pulsing power to the heater to heat the capillary passage as the fluid passes through the capillary passage, the fluid being volatilized and forming the aerosol within the mouthpiece.

18. The method for generating an aerosol as recited in claim 14, wherein the reservoir containing a medicament which is volatilized and supplied to the interior of the mouthpiece.

19. The method for generating an aerosol as recited in claim 14, wherein the aerosol generator includes a controller monitoring a parameter of the heater and controlling supply of power to the heater to maintain the heater at a desired temperature range while fluid passes through the capillary passage, the fluid being volatilized so as to form the aerosol.

20. The method for generating an aerosol as recited in claim 14, wherein the aerosol being supplied to the interior of the mouthpiece by supplying power to the heater, closing the first valve, opening the second and third valves, removing fluid from the metering chamber, supplying a predetermined volume of fluid to the capillary passage and volatilizing the fluid in the capillary passage.

21. The method for generating an aerosol as recited in claim 20, the method comprising rotating the camshaft to a first position at which the first valve is closed and the second and third valves are open to effect delivery of a predetermined volume of fluid to the capillary passage during an aerosol delivery cycle, further rotating the camshaft to a second position at which the second and third valves are closed and the first valve opens to effect delivery of fluid from the reservoir to the metering chamber during a fill cycle.

22. The method for generating an aerosol as recited in claim 14, wherein the reservoir contains at least 10 doses of a medicated fluid, the method further comprising filling the metering chamber with a predetermined volume of the medicated fluid by delivering a volume of the medicated fluid from the reservoir to the capillary passage, heating the capillary passage to volatilize the predetermined volume of the medicated fluid, and forming the aerosol by admixing the vaporized fluid with air in the interior of the mouthpiece.

23. The method for generating an aerosol as recited in claim 22, wherein the aerosol generator includes a displacement piston, the method including moving the displacement piston from a first position at which the metering chamber is filled with fluid to a second position at which the displacement piston deflects an elastomeric wall of the metering chamber.

24. The method for generating an aerosol as recited in claim 14, wherein the interior of the mouthpiece is supplied air only through the air passage, the valve being closed during sensing of the pressure drop and the valve being opened within a predetermined period after sensing of the pressure drop after which the aerosol is supplied to the interior of the mouthpiece.

25. An aerosol generator comprising:

a mouthpiece having an outlet through which aerosol is supplied to a user of the aerosol generator;

an aerosol generator system operable to supply aerosol to an interior of the mouthpiece, the aerosol generating system comprising a capillary sized flow passage and a heater arranged to volatilize liquid in the flow passage so as to produce the aerosol in the interior of the mouthpiece;

an air passage through which air is supplied to the interior of the mouthpiece;

a pressure sensor operable to output a signal upon detection of a drop in pressure in the interior of the mouthpiece;

a controller operable to activate the aerosol generator system to delivery aerosol to the interior of the mouthpiece in response to output of the signal by the pressure sensor;

a valve operable to open and close the air passage, the controller being operable to open the valve in response to output of the signal by the pressure sensor; and a dispensing member and a metering chamber, the metering chamber comprising a recess and an elastomeric wall covering the recess, the dispensing member being movable from a first position relative to the elastomeric wall to a second position at which the elastomeric wall is deformed into the recess, the metering chamber providing fluid communication between a source of fluid and the flow passage, and the dispensing member being movable in a manner which provides a substantially constant flow rate of the fluid in the flow passage;

wherein the aerosol generator is a hand-held inhaler.

26. The aerosol generator as recited in claim 25, wherein the aerosol generator includes a housing and a cap slidably attached to the housing, the cap including the mouthpiece at one end thereof, the cap being slidable from an off position at which aerosol is prevented from being delivered to the interior of the mouthpiece to an aerosol delivery position at which the aerosol generating system is in a breath actuation mode allowing the user to obtain a dose of aerosol by inhaling on the outlet.

27. An aerosol generator comprising:

a metering chamber comprising a recess in a first layer of material and an elastomeric layer overlying the recess, the first layer of material including an inlet, a first channel extending between the inlet end the metering chamber, an outlet and a second channel extending between the metering chamber and the outlet, the elastomeric layer covering the inlet, the first channel, the second channel and the outlet;

a dispensing member movable from a first position relative to the elastomeric layer to a second position at which the elastomeric layer is deformed into the recess;

a flow passage in fluid communication with the metering chamber;

a mouthpiece having an interior thereof in fluid communication with an outlet of the flow passage;

a heater in heat transfer communication with at least a portion of the flow passage, the heater being operable to volatilize fluid in the flow passage such that volatilized fluid forms an aerosol in the interior of the mouthpiece.

28. The aerosol generator as recited in claim 27, wherein the aerosol generator includes a housing and a cap slidably attached to the housing, the cap including the mouthpiece at one end thereof, the cap being slidable from an off position at which aerosol is prevented from being delivered to the interior of the mouthpiece to an aerosol delivery position at which the aerosol generator is in a breath actuation mode allowing the user to obtain a dose of aerosol by inhaling on the outlet.

29. The aerosol generator as recited in claim 27, further comprising a controller electrically operating an actuating mechanism which moves the dispensing member from the first position to the second position so as to provide a substantially constant flow rate of a predetermined volume of fluid through the flow passage.

30. The aerosol generator as recited in claim 27 further comprising first and second plungers, the first plunger being movable from a first position at which the inlet is open to a second position at which the elastomeric layer is pressed against a first valve seat so as to close the inlet, and the second plunger being movable from a first position at which the outlet is open to a second position at which the elastomeric layer is pressed against a second valve seat so as to close the outlet.

31. The aerosol generator as recited in claim 30, further comprising an actuating mechanism which moves the first plunger to the second position while maintaining the second plunger in the first position.

32. An aerosol generator comprising:
 a mouthpiece having an outlet through which aerosol is supplied to a user of the aerosol generator;
 an air passage through which air is supplied to an interior of the mouthpiece;
 a sensor operable to output a signal upon detection of a pressure drop in the interior of the mouthpiece;
 a housing;
 a capillary passage disposed within the housing;
 a heater disposed within the housing;
 a reservoir disposed within the housing;
 a metering chamber disposed within the housing, the metering chamber being supplied fluid from the reservoir by a first flow passage and the capillary passage being supplied fluid from the metering chamber by a second flow passage;
 a power source adapted to supply electrical power to the heater, the heater arranged to volatilize liquid in the capillary passage to produce aerosol in the interior of the mouthpiece;
 a controller operable to activate the aerosol generator to deliver aerosol to the interior of the mouthpiece in response to output of the signal by the sensor;
 a first valve adapted to open and close the first flow passage, the controller being operable to open the first valve in response to output of the signal by the sensor; a second valve adapted to open and close the second flow passage; and a third valve adapted to open and close the air passage.

* * * * *